(12) United States Patent
Walsh

(10) Patent No.: US 9,460,050 B2
(45) Date of Patent: Oct. 4, 2016

(54) RACE PROGRESS APPARATUS

(76) Inventor: Duncan Christopher Walsh, Nottingham (GB)

(*) Notice: Subject to any disclaimer, the term of this patent is extended or adjusted under 35 U.S.C. 154(b) by 514 days.

(21) Appl. No.: 13/639,715

(22) PCT Filed: Apr. 5, 2011

(86) PCT No.: PCT/GB2011/000521
§ 371 (c)(1),
(2), (4) Date: Feb. 19, 2013

(87) PCT Pub. No.: WO2011/124878
PCT Pub. Date: Oct. 13, 2011

(65) Prior Publication Data
US 2013/0142377 A1    Jun. 6, 2013

(30) Foreign Application Priority Data
Apr. 7, 2010 (GB) .................................. 1005732.1

(51) Int. Cl.
| | | |
|---|---|---|
| *G06F 17/00* | (2006.01) | |
| *G06F 19/00* | (2011.01) | |
| *H04R 1/10* | (2006.01) | |
| *A63B 71/06* | (2006.01) | |
| *A63B 33/00* | (2006.01) | |
| *A63B 69/06* | (2006.01) | |
| *A63B 69/16* | (2006.01) | |
| *A63B 69/00* | (2006.01) | |
| *H04R 5/033* | (2006.01) | |
| *A63B 24/00* | (2006.01) | |

(52) U.S. Cl.
CPC .............. *G06F 17/00* (2013.01); *A63B 33/00* (2013.01); *A63B 71/0622* (2013.01); *A63B 71/0686* (2013.01); *G06F 19/3481* (2013.01); *H04R 1/10* (2013.01); *A63B 24/0075* (2013.01); *A63B 69/0028* (2013.01); *A63B 69/06* (2013.01); *A63B 69/16* (2013.01); *A63B 2071/063* (2013.01); *A63B 2071/0625* (2013.01); *H04R 5/033* (2013.01)

(58) Field of Classification Search
None
See application file for complete search history.

(56) References Cited

U.S. PATENT DOCUMENTS

| | | | |
|---|---|---|---|
| 7,534,206 B1 | 5/2009 | Lovitt et al. | |
| 7,572,205 B1* | 8/2009 | Cribar | ............................... 482/3 |
| 7,927,253 B2 | 4/2011 | Vincent et al. | |
| 8,000,822 B2 | 8/2011 | Shirai et al. | |
| 2005/0195094 A1* | 9/2005 | White | ..................... 340/870.01 |
| 2005/0288154 A1* | 12/2005 | Lee et al. | .......................... 482/3 |
| 2006/0136173 A1* | 6/2006 | Case et al. | ..................... 702/182 |
| 2007/0146116 A1* | 6/2007 | Kimbrell | ..................... 340/5.52 |
| 2009/0097689 A1* | 4/2009 | Prest et al. | .................... 381/380 |

FOREIGN PATENT DOCUMENTS

WO    2009067837    6/2009

OTHER PUBLICATIONS

Stack Overflow "Generating random integers in a range with Java." Dec. 12, 2008. pp. 1-12. http://stackoverflow.com/questions/363681/generating-random-integers-in-a-range-with-java.*
Cycling Weekly, "MI-Sport Waterproof MP3 Player/Headphones." Apr. 18, 2008. pp. 1-9.*
International Search Report and Written Opinion for PCT/GB2011/000521, Mar. 26, 2012.
Garmin "Forerunner 405CX Owner's Manual" Internet Citation, Mar. 1, 2009.
Polar Electro Oy "Polar RS200 User Manual" Jan. 1, 2005.

* cited by examiner

*Primary Examiner* — Curtis Kuntz
*Assistant Examiner* — Qin Zhu
(74) *Attorney, Agent, or Firm* — Meyertons, Hood, Kivlin, Kowert & Goetzel, P.C.; Eric B. Meyertons

(57) ABSTRACT

A portable unit usable by a person when carrying out an exercise. The unit is programmable with details of a virtual athlete and their performance in a specific race, to enable the user to race against the virtual athlete. The unit informs the user through headphones of the progress of the virtual athlete during a race being carried out by a user. The unit may also be programmable with periodic encouragement messages for a user.

3 Claims, No Drawings

RACE PROGRESS APPARATUS

This invention concerns a race progress apparatus.

A number of race progress apparatus are currently available. Many of these include a GPS to locate the position and progress of a user. A GPS is often not sufficiently accurate in race scenarios, and also adds significantly to the cost of any unit. In a number of instances, as for example when swimming, a GPS is generally not usable. Also with stationary exercising in a gym or elsewhere such as using a running machine or cycle trainer, a GPS is not usable nor appropriate.

In many instances though athletes in training would wish information and/or encouragement during their training to imitate race conditions, and also to provide more interest. For example, it could be very useful for swimmers to receive reminders about maintaining their technique and form, which often deteriorate with fatigue.

According to a first aspect of the invention there is provided a portable unit usable by a person when carrying out an exercise, the unit being programmable with details of a virtual athlete and their performance in a specific race, to enable the user to race against the virtual athlete, with the unit informing the user of the progress of the virtual athlete during a race being carried out by a user.

The unit may inform the user of the virtual athlete's progress at set time periods and/or particular stages in a race. The unit may be configured to provide an indication of the virtual athlete's progress upon request by a user, and one or more controls may be provided on the unit to enable such a request to be made.

The unit may enable in one mode the input of the virtual athlete's finish time for a race, and may enable input of one or more split times for the race. In a further mode the unit enables the input of the virtual athlete's finish time for a race within a range, and the unit will choose at random the actual finish time within the range for a specific race. The unit may enable input of one or more split times for the virtual athlete in a race within a range, with the actual split times being chosen at random within the respective range, by the unit.

The unit may be configured such that information provided by the unit to a user may be programmable, and could be programmable to indicate the progress of the virtual athlete at set time periods.

The unit may be configured such that it can be programmed to provide encouragement messages, which messages can be personalised by a user and provided at required programmable intervals.

According to a second aspect of the invention there is provided a portable unit usable by a person when carrying out an exercise, the unit being programmable to provide encouragement messages, which messages can be personalised by a user and provided at required programmable intervals.

In one embodiment the unit is wearable by a user when carrying out exercise. The unit may provide audible messages, and the unit may also incorporate a digital sound player which may be in an MP3 format, to enable a user to listen to music when messages are not given by the unit.

The unit may be configured such that when the unit gives messages these interrupt the playing of the digital sound player.

The unit may include a set of headphones, and the unit may be incorporated within a casing of the headphones. The casing and headphones may be waterproof so that the apparatus is usable by a person swimming.

In an alternative embodiment the unit includes a screen to provide messages to a user. The unit may be mountable on a bike, and/or wearable by a user.

Embodiments of the present invention will now be described by way of example only.

In a first embodiment a unit according to the invention is provided for use in swimming. A set of waterproof headphones is provided. Incorporated within the casing of the headphones is an MP3 player and a programmable race progress unit. Controls are provided on the exterior of the headphones to enable control of the MP3 player. A socket is provided on the unit to enable programming of the race progress unit when connected to a computer prior to the swim.

The unit is configured such that music from the MP3 player can be heard by a user except when messages are being received from the unit. The MP3 player can be controlled in any conventional manner as required.

The unit permits input relating to a virtual athlete in a race, and for instance in this embodiment this may be a swimming race. The time and/or length of the race may be entered, and this could be in terms of distance and/or the number of lengths.

A finish time for the virtual athlete can be entered. This can be entered in one of two modes. In a first mode the precise finish time can be entered, and also if required one or more split times can be entered. These split times could reflect for instance a person with a sprint finish or a sprint start to a race or other characteristics where they are likely to perform at different speeds during the race.

In a second mode the finish time for the virtual athlete can be entered within a range, and for a race the unit will choose at random an actual finish time for the virtual athlete within the range, which time will not be known by a user. One or more split times can be entered in a similar manner as a range of split times, with the unit choosing the particular split time.

When the user starts the race he will obviously activate the unit. The unit can be programmed as required to provide an indication of the virtual athlete's progress, for example when particular split times such as particular distances or number of lengths are reached. At these times an audible indication will be given to the user. This could for instance interrupt music being listened to on the MP3 player.

In addition or as an alternative, the unit can be programmed to provide encouragement or other messages to the user. For instance the messages could simply be to encourage the person to keep going, or could indicate that a particular time period has elapsed. Such messages could be given by the person themselves, or perhaps a personal trainer or other person.

As the user will know their position by virtue of the number of lengths they have completed, when an indication of the position of the virtual athlete is received, the user can then compare this with the position they are in when the message is received, and will know for instance whether they are ahead or behind the virtual athlete.

As an example, a swimmer is racing over 30 lengths of a 25 m pool, and his usual time to complete such a race is around 22 minutes. He then sets the device so that the virtual athlete will finish the race at a time of between 21 and 23 minutes. The device will then at random calculate the finish time without telling the user, and for instance could choose a time of 21 minutes 11 seconds.

In the light of this time the unit calculates an average speed. The unit may if required vary the virtual athlete's speed along the length of the course within a range, but so as to ensure that the virtual athlete will finish in exactly 21 minutes and 11 seconds. Once the user has indicated that they have started the race the unit will run, and inform via the headphones how many lengths the virtual athlete has completed. As the user knows how many lengths they will have competed, they can compare their progress relative to the virtual athlete.

In a second embodiment a unit is to be used by an athlete whilst running. A similar unit as described above may be used, or a different unit may be used which for instance may not be waterproof. The waterproof feature is though usable with athletes generally, in view of the sweat they will produce in a race. The unit could have all the components maintained within the headphone casing, or a separate unit could be provided being worn by the user. A separate unit could be connected by a wire to the headphones, or a wireless connection using a Bluetooth® connection could be provided.

This unit could be used in the following scenario. A racer wants to be paced through a 5 km run to achieve a time of less than 18 minutes. The race is carried out on a running track so the user will know his position. The user sets the unit to have an exact finish time of 17 minutes and 57 seconds. The user also knows that he needs to reach the 3 km mark in 10 minutes 30 seconds as his fourth 1000 m is generally his slowest.

He therefore programs the unit so that the virtual athlete will reach the 3 km point in 10 minutes 30 seconds, at which time a message will be received to indicate that the virtual athlete has reached this point. The user will then know whether he has to speed up or not to achieve his goal, by comparing his own position at that time. The unit may be programmed to indicate when the virtual athlete finishes some or all of the laps.

For both of the above scenarios use of a GPS would not be possible or wholly accurate in maintaining the position of the user. Generally a GPS would generally not be possible to use in a swimming pool, and a user can in any case monitor the number of lengths they have covered. On a running track a GPS would not be wholly accurate, nor for instance would be counting the number of strides an athlete takes. Therefore by knowing the number of laps and the position within each lap, the user can know how they are performing relative to their target. Using a finishing time within a range, helps to simulate race conditions where athletes may perform differently at different times.

The unit could be programmed with a number of events for instance to run concurrently, such as in the event of a biathlon or triathlon. The unit can be alternatively or additionally programmed to provide general encouragement messages which may simply be encouraging or could for instance be humourous. The encouragement messages could be used as instructions for a workout, e.g. "OK 1 minute sprints" or "1 minute press ups" etc. This could be programmed at particular times, and particularly knowing when an athlete may require additional encouragement.

In a further embodiment a unit is provided with a readable screen. This could be a unit for cyclists which would fit on a bike, and would have a screen readable by a cyclist, rather than have headphones and an MP3 player, which could be dangerous when cycling. As most bikes are fitted or can readily be fitted with a device to indicate the distance traveled, this will indicate to a user the distance traveled in a race, with the unit being used to indicate their progress against a virtual athlete along the lines indicated above. Such a unit could be provided quite inexpensively, but significantly prove the cycling experience and assist in training for races, or simply provide additional enjoyment or novelty to training.

For use in combined sports such as triathlons, the unit could also be worn by an athlete whilst running and/or swimming. A version could be produced with a screen to be worn on the wrist whilst running. If the unit is waterproof, additionally or alternatively it could also be worn whilst swimming.

There are thus described a number of embodiments according to the invention enabling different athletes to monitor their performance and race against a virtual athlete, with the performance of the virtual athlete being programmable, either precisely or within particular ranges. The units allow monitoring of an athlete's performance where their position is known or can be readily determined by virtue of their position on a track or in a swimming pool, or for instance by an odometer on a bicycle.

The embodiments operate without the requirement for a GPS. Accordingly they are suitable for indoor and gym based training activities. For example, a unit could be used on a running machine. As the running machine will indicate the distance traveled, this will indicate the user's position relative to a virtual athlete. Units according to the invention could also be used on an exercise bike where again the apparent distance traveled will be indicated, or perhaps on a rowing machine.

The embodiments allow users, their personal trainers or others to pre-set unique instructions, encouragements or other messages. When for instance music is being listened to, this can be interrupted by such messages at specially designated times.

A wide range of other modifications may be made without departing from the scope of the invention. For instance any combination of the above features may be provided.

The invention claimed is:

1. A set of headphones wearable by a person when carrying out exercise comprising:
   a programmable race progress unit incorporated into a casing of the set of headphones, the programmable race progress unit comprising a processor and an input, wherein the programmable race progress unit processor is programmable via the input to provide unique audible encouragement messages, messages of instruction, and messages of time elapsed, which messages can be personalized by a user and provided at required programmable intervals; and
   a digital sound player incorporated into the casing of the set of headphones to enable a user to listen to music when messages are not given by the unit;
   the programmable race progress unit and the digital sound player being separate electrical components incorporated within the casing of the set of headphones;
   wherein the programmable race progress unit processor is configured such that when the unit gives encouragement messages, messages of instruction, and messages of time elapsed, the programmable race progress unit processor sends an interrupt signal to the digital sound player to interrupt the playing of the digital sound player.

2. The portable unit according to claim 1, in which the digital sound player is capable of playing sound files in MP3 format.

3. The portable unit according to claim 1, in which the casing and headphones are waterproof.

* * * * *